United States Patent
Takeno et al.

(10) Patent No.: US 9,933,246 B2
(45) Date of Patent: Apr. 3, 2018

(54) OPTICAL COHERENCE TOMOGRAPHY DEVICE

(71) Applicant: NIDEK CO., LTD., Aichi (JP)

(72) Inventors: Naoki Takeno, Gamagori (JP); Masaaki Hanebuchi, Gamagori (JP); Yasuhiro Furuuchi, Gamagori (JP); Hajime Namiki, Gamagori (JP)

(73) Assignee: NIDEK CO., LTD., Aichi (JP)

( * ) Notice: Subject to any disclaimer, the term of this patent is extended or adjusted under 35 U.S.C. 154(b) by 337 days.

(21) Appl. No.: 14/566,778

(22) Filed: Dec. 11, 2014

(65) Prior Publication Data

US 2015/0168127 A1    Jun. 18, 2015

(30) Foreign Application Priority Data

Dec. 13, 2013   (JP) ................................ 2013-258410

(51) Int. Cl.
*G06K 9/00* (2006.01)
*A61B 5/00* (2006.01)
(Continued)

(52) U.S. Cl.
CPC ........ *G01B 9/02091* (2013.01); *A61B 3/0025* (2013.01); *A61B 3/102* (2013.01);
(Continued)

(58) Field of Classification Search
None
See application file for complete search history.

(56) References Cited

U.S. PATENT DOCUMENTS

2012/0120408 A1* 5/2012 Yasuno ................ A61B 3/102
356/479
2012/0277579 A1 11/2012 Sharma et al.
(Continued)

FOREIGN PATENT DOCUMENTS

WO    20100143601 A1    12/2010
WO    2012170722 A2    12/2012

OTHER PUBLICATIONS

Search Report dated May 12, 215 issued by the European Patent Office in counterpart European Patent Application No. 14197600.1.
(Continued)

*Primary Examiner* — Matthew Bella
*Assistant Examiner* — Jose M Torres
(74) *Attorney, Agent, or Firm* — Sughrue Mion, PLLC

(57) ABSTRACT

There is provided an optical coherence tomography device provided with: an OCT optical system configured to output OCT signal; and an analysis processing unit configured to process the OCT signal and generate motion contrast data of the specimen. The analysis processing unit is provided with: a first image data generation unit configured to process multiple OCT signals to generate first image data representing phase difference information of the multiple OCT signals, and a second image data generation unit configured to process the OCT signal to generate second image data representing amplitude information of the OCT signal. The analysis processing unit generates the motion contrast data based on the phase difference information in the first image data and the amplitude information in the second image data.

3 Claims, 13 Drawing Sheets

(51) Int. Cl.
  *G01B 9/02* (2006.01)
  *A61B 3/10* (2006.01)
  *A61B 3/00* (2006.01)

(52) U.S. Cl.
  CPC .......... *A61B 5/0066* (2013.01); *A61B 5/7203* (2013.01); *G01B 9/0201* (2013.01); *G01B 9/02045* (2013.01); *G01B 9/02087* (2013.01); *G06T 2207/10101* (2013.01)

(56) References Cited

U.S. PATENT DOCUMENTS

| | | | |
|---|---|---|---|
| 2012/0316434 A1 | 12/2012 | Yun et al. | |
| 2013/0039557 A1* | 2/2013 | Wei | G06K 9/00214 382/131 |
| 2013/0176532 A1* | 7/2013 | Sharma | A61B 3/102 351/206 |
| 2013/0188196 A1* | 7/2013 | Kang | G01B 9/02091 356/479 |
| 2013/0275051 A1* | 10/2013 | Farhat | C12M 41/46 702/19 |
| 2014/0221827 A1 | 8/2014 | Motaghiannezam et al. | |
| 2014/0228681 A1* | 8/2014 | Jia | G01B 9/02091 600/425 |
| 2015/0092195 A1* | 4/2015 | Blatter | G01B 9/02091 356/479 |

OTHER PUBLICATIONS

Adrian Mariampillai, et al.; "Speckle Variance Detection of Microvasculature Using Swept-Source Optical Coherence Tomography"; Optic Letters; vol. 33 No. 13; Jul. 1, 2008; pp. 1530-1532.

Yonghua Zhao; et al.; "Phase-Resolved Optical Coherence Tomography and Optical Doppler Tomography for Imaging Blood Flow in Human Skin With Fast Scanning Speed and High Velocity Sensitivity"; Optics Letters; vol. 25 No. 2; Jan. 15, 2000; pp. 114-116.

Vivek Srinivasan, et al.; "Rapid Volumetric Angiography of Cortical Microvasculature With Optical Coherence Tomography"; Optics Letters; vol. 35 No. 1; Jan. 1, 2010; pp. 43-45.

* cited by examiner

FIG. 5A
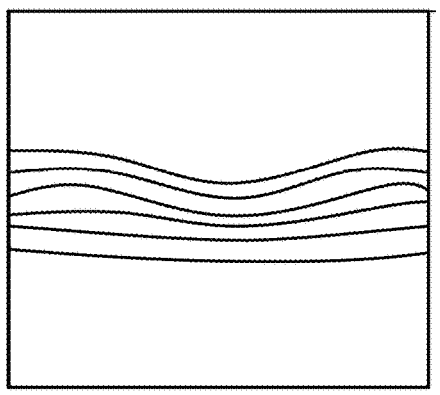 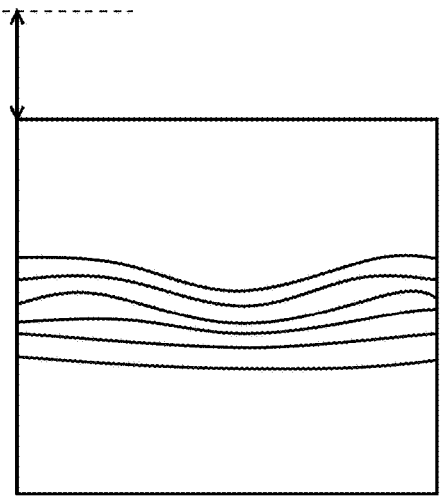
FIG. 5B
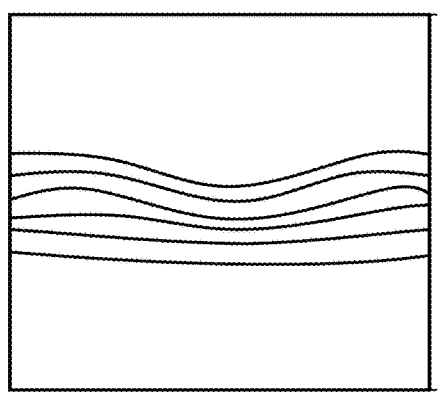 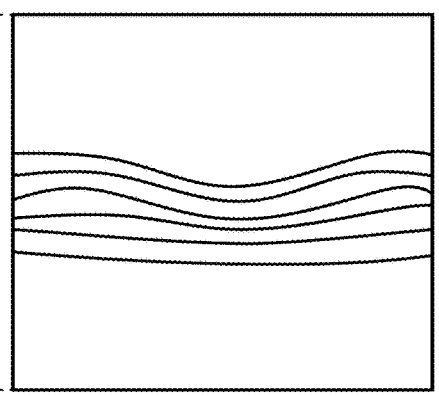

OPTICAL COHERENCE TOMOGRAPHY DEVICE

CROSS-REFERENCE TO RELATED APPLICATION

This application claims priority from Japanese Patent Application No. 2013-258410, filed on Dec. 13, 2013, the entire subject matter of which is incorporated herein by reference.

TECHNICAL FIELD

The present disclosure relates an optical coherence tomography device that obtains motion contrast data of a specimen.

BACKGROUND

In the related art, as a device which performs angiography, for example, a fundus camera, a scanning laser optometry device, or the like has been known. In using this type of devices, a contrast agent which emits light with specific excitation light is injected into a body of a specimen. The device receives light from the contrast agent to obtain an angiographic image. That is, in the related art, the injection of the contrast agent is required.

In recent years, a device which obtains motion contrast by applying an optical coherence tomography (OCT) technique without using a contrast agent has been suggested as described in the following related-art documents.
Patent Document 1:
  International Patent Publication No. 2010/143601
Non-Patent Document 1:
  Yonghua Zhao et al. OPTICS LETTERS/Vol. 25, No. 2/Jan. 15, 2000
Non-Patent Document 2:
  Adrian Mariampillai et al. OPTICS LETTERS/Vol. 33, No. 13/Jul. 1, 2008
Non-Patent Document 3
  Vivek J. Srinivasan et al. OPTICS LETTERS/Vol. 35, No. 1/Jan. 1, 2010

However, it is considered that a technique for obtaining a functional OCT image, such as motion contrast, using OCT is still developing and stands further improvement.

SUMMARY OF THE INVENTION

The present disclosure has been made in view of the above circumstances, and one of objects of the present disclosure is to provide an optical coherence tomography device capable of acquiring a satisfactory functional OCT image in consideration of the above-described problems.

According to an illustrative embodiment of the present disclosure, there is provided an optical coherence tomography device that is provided with: an OCT optical system configured to detect measurement light irradiated onto a specimen and a reference light and output OCT signal based on the measurement light and the reference light; and an analysis processing unit configured to process the OCT signal and generate motion contrast data of the specimen. The analysis processing unit is provided with: a first image data generation unit configured to process multiple OCT signals which is a plurality of OCT signals output from the OCT optical system being obtained at a different timing for the same position on the specimen and to generate first image data representing phase difference information of the multiple OCT signals; and a second image data generation unit configured to process the OCT signal output from the OCT optical system to generate second image data representing amplitude information of the OCT signal. The analysis processing unit is configured to generate the motion contrast data based on the phase difference information in the first image data generated by the first image data generation unit and the amplitude information in the second image data generated by the second image data generation unit.

According to another illustrative embodiment of the present disclosure, there is provided an optical coherence tomography device that is provided with: an OCT optical system configured to detect measurement light irradiated onto a specimen and a reference light and output OCT signal based on the measurement light and the reference light; and an analysis processing unit configured to process the OCT signal and generate functional OCT data of the specimen. The analysis processing unit is provided with: a first image data generation unit configured to generate first functional OCT image data by applying first analysis processing on the OCT signal; and a second image data generation unit configured to generate at least one of OCT image data or second functional OCT image data by applying second analysis processing that is different from the first analysis processing on the OCT signal. The analysis processing unit is configured to generate the functional OCT image data based on the first functional OCT image data generated by the first image data generation unit and at least one of the OCT image data and the second functional OCT image data generated by the second image data generation unit.

According to another illustrative embodiment of the present disclosure, there is provided a method for controlling an optical coherence tomography device being provided with an OCT optical system configured to detect measurement light irradiated onto a specimen and a reference light and output OCT signal based on the measurement light and the reference light. The method includes: processing multiple OCT signals which is a plurality of OCT signals output from the OCT optical system being obtained at a different timing for the same position on the specimen and to generate first image data representing phase difference information of the multiple OCT signals; processing the OCT signal output from the OCT optical system to generate second image data representing amplitude information of the OCT signal; and generating the motion contrast data based on the phase difference information in the first image data and the amplitude information in the second image data.

BRIEF DESCRIPTION OF THE DRAWINGS

In the accompanying drawings:
FIGS. 5A and 5B are diagrams illustrating image deviation.

DETAILED DESCRIPTION

Figure 1:
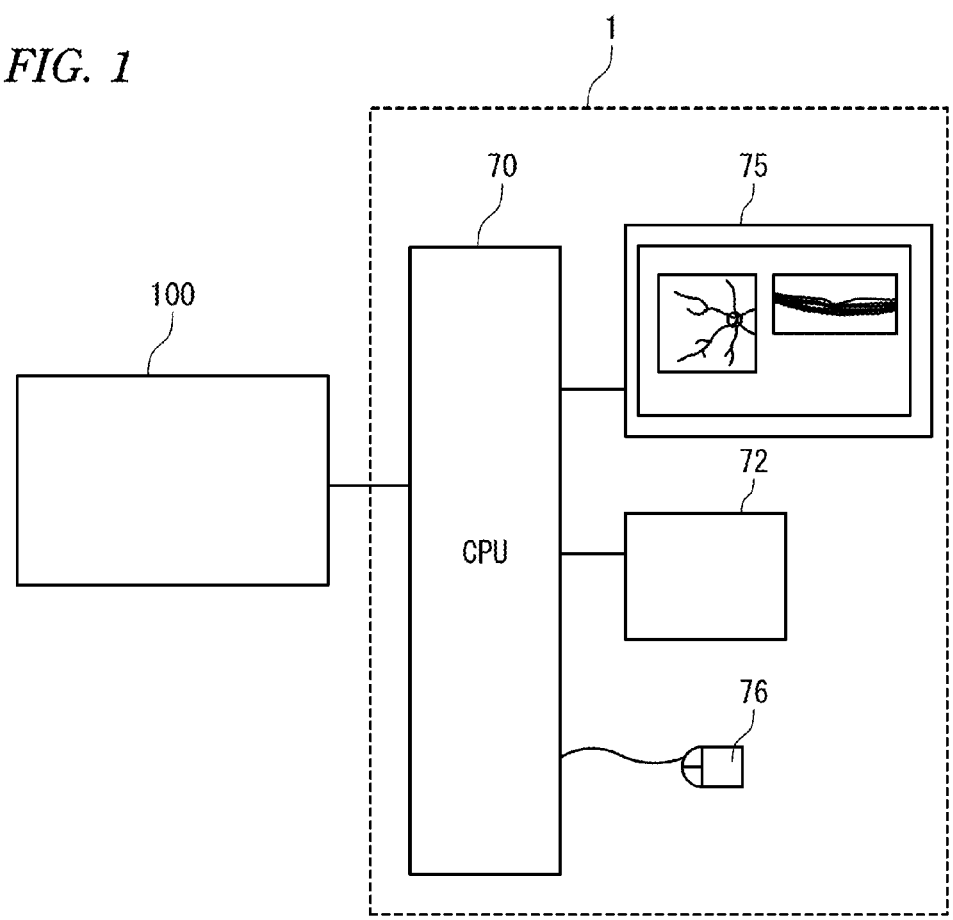
FIG. 1 is a block diagram illustrating a configuration of an optical coherence tomography device.
Figure 2:
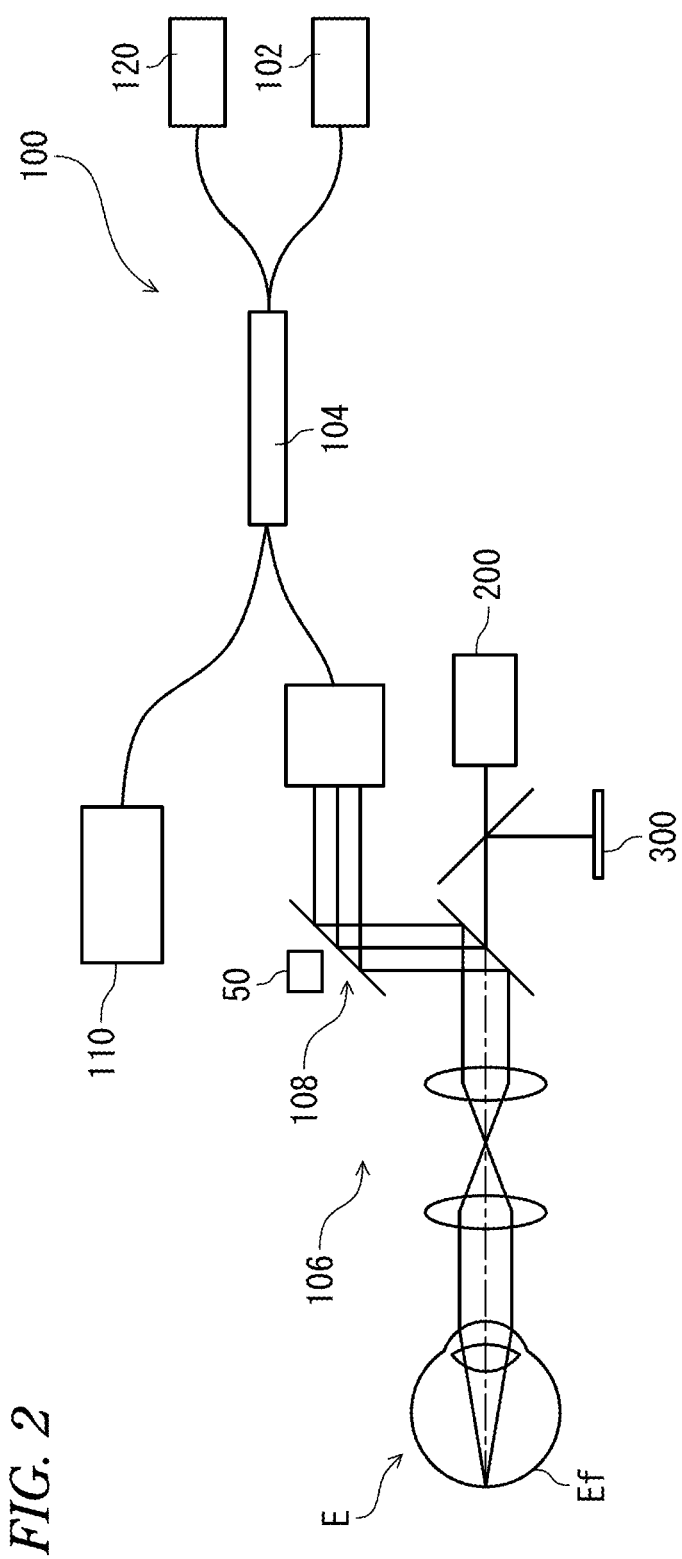
FIG. 2 is a diagram showing an outline of an optical system.

Hereinafter, an overview of an illustrative embodiment according to the present invention will be described.

<Composition of Functional OCT Image>

An optical coherence tomography device 1 is provided with an OCT optical system (OCT interferometer) 100 and an analysis processing unit (for example, a control unit 70).

The OCT optical system 100 may be configured to detect measurement light irradiated onto a specimen and a reference light and output OCT signal based on the measurement light and the reference light.

The analysis processing unit may be configured to process the OCT signal to generate functional OCT image data in the specimen. The analysis processing unit may be provided with a first OCT image data generation unit and a second OCT image data generation unit. For example, the first OCT image data generation unit may be configured to generate first functional OCT image data by first analysis processing on the OCT signal. For example, the second OCT image data generation unit may be configured to generate OCT image data or second functional OCT image data by second analysis processing different from the first analysis processing on the OCT signal.

For example, the analysis processing unit may be configured to generate a new functional OCT image based on first functional OCT image data and second functional OCT image data. With this, for example, it may be possible to obtain functional OCT image data with high contrast and removed unnecessary reflective components compared to individual functional OCT image data.

Functional OCT image data may be, for example, image data based on a Doppler OCT image (phase difference image) of Phase Difference, Phase variance, Doppler variance, or the like, image data based on a vector difference (VD) of a complex OCT signal, image data based on Decorrelation of an intensity signal, image data representing variation in intensity, such as Spectral variance, in the form of an image, or the like. For example, functional OCT image data may be acquired by processing various OCT signals acquired from Scattering OCT, Polarization Sensitive OCT, Stereoscopic OCT, or the like. Functional OCT image data may be image data or signal data.

The functional OCT image data may be complex image data such as image data containing real part and imaginary part of the complex OCT signal.

For example, when the analysis processing unit generates a new functional OCT image based on first functional OCT image data and second functional OCT image data, functional OCT image data acquired by different analysis methods may be used as first functional OCT image data and second functional OCT image data. For example, image data based on a Doppler OCT image may be used as first functional OCT image data, and image data based on a polarization sensitive OCT image may be used as second functional OCT image data. For example, image data based on a Scattering OCT image may be used as first functional OCT image data, and image data based on a Stereoscopic OCT image may be used as second functional OCT image data.

Various combinations are used as a combination of first functional OCT image data and second functional OCT image data generated by different types of analysis processing.

The analysis processing unit may be configured to generate a new functional OCT image based on first functional OCT image data and OCT image data. As OCT image data, for example, image data representing the magnitude of the amplitude of the OCT signal in the form of an image, image data representing the intensity (a value obtained by squaring the magnitude of the amplitude) of the OCT signal, or the like may be used.

<Generation of Motion Contrast>

The optical coherence tomography device 1 may be configured to calculate motion contrast of a sample by two or more methods from at least two temporally different detection signals at the same position as a functional OCT image. A combination of the results based on motion contrast may be set as a sample image.

As a method of calculating motion contrast of the sample from the acquired complex OCT signal, for example, there is a method using a phase difference (PD) of a complex OCT signal (e.g. see Non-Patent Document 1 for details; hereinafter, referred to as a Doppler phase method or a PD method), a method using a vector difference (VD) of a complex OCT signal (e.g. see Non-Patent Document 3 for details; hereinafter, referred to as a vector difference method or a VD method), a method using spectral variance (SV) (e.g. see Non-Patent Document 2 for details; hereinafter, referred to as a SV method), or the like.

The PD method calculates fluctuation in phase of a complex OCT signal, that is, a phase difference to calculate motion contrast of a sample. For example, the phase difference is calculated by Expression (3), which is described later.

Figure 10:
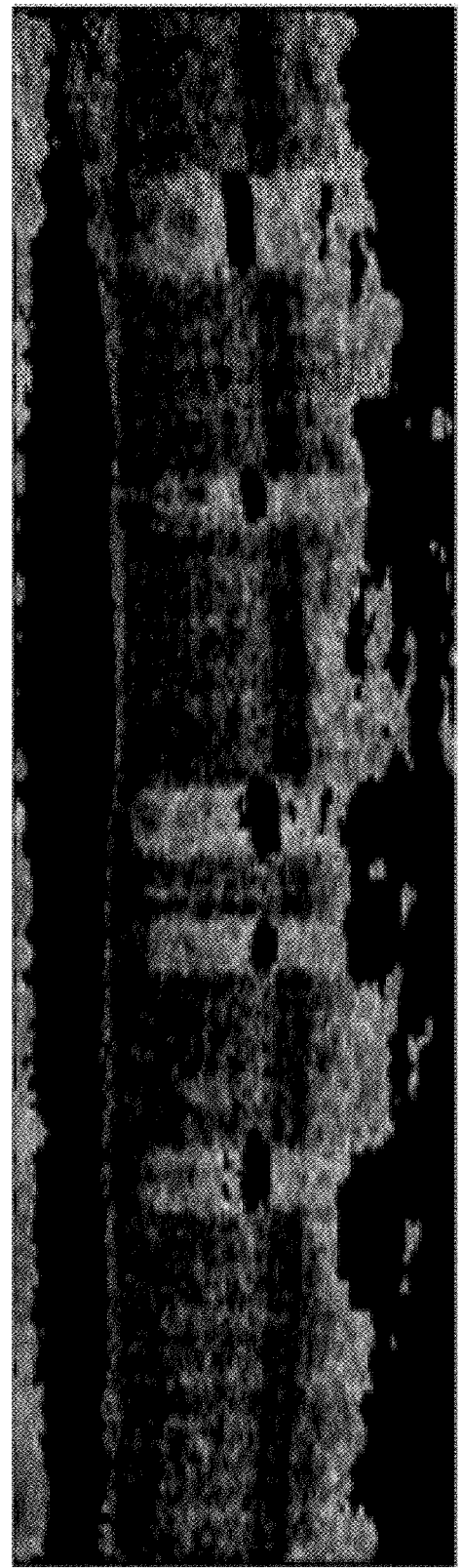
FIG. 10 is a diagram showing an image obtained by a Doppler phase method.

For example, an advantage of the PD method is that a signal with high reflection in a nerve fiber layer (NFL) or a retinal pigment epithelium (RPE) with no variation in phase is hardly detected because only a phase difference is viewed. A disadvantage of the PD method may be that an artifact (a signal undesired to be detected) is detected by the influence of a blood vessel in a part in contact with the shadow of the blood vessel (see FIG. 10).

In the VD method, fluctuation in complex vector of a complex OCT signal, that is, a vector difference is calculated to calculate motion contrast of a sample. For example, the vector difference is calculated by Expression (5). For example, the amplitude of a complex OCT signal may have an influence on fluctuation in complex vector.

For example, an advantage of the VD method is that a signal of a blood vessel becomes large and contrast is satisfactory because both amplitude and phase are used. A disadvantage of the VD method may be that a signal in a high reflection part, such as an NFL, becomes large.

In the SV method, fluctuation in intensity of a complex OCT signal, that is, variation of intensity is calculated to calculate motion contrast of a sample.

A disadvantage of the SV method may be that an artifact is detected in a high reflection part because only intensity is viewed.

In this example, it is possible to skillfully use different advantages of the respective computation methods by combining motion contrast of the sample computed by two or more methods described above.

For example, using two methods of the PD method and the VD method, the control unit 70 detects a signal which has fluctuation in phase and fluctuation in complex vector. Since a vascular part has large fluctuation in phase and large fluctuation in complex vector, the control unit 70 can skillfully detect a signal from the vascular part.

Doppler optical coherence tomography (referred to as DOCT) is means for obtaining a rate of a blood flow or the like on the condition that the amount of temporal change in phase (change in frequency) obtained by Fourier transform of spectrum interference information corresponds to moving speed of a subject as a Doppler signal (see Patent Document 1). In OCT, wavelength scanning OCT (time domain OCT), Fourier domain OCT, or the like can be applied.

For example, Doppler OCT is means for irradiating a predetermined region of a specimen with measurement light twice at the time $\Delta t$ so as to measure a blood flow rate of the predetermined region of the specimen, obtaining the amount $\Delta \varphi$ of temporal change in phase (hereinafter, simply referred to as an amount of change in phase or a phase difference) from the thus-obtained two tomographic images, calculating the amount of temporal change in frequency (hereinafter, referred to as a frequency shift) from the amount $\Delta \varphi$ of change in phase, and calculating and obtaining a blood flow rate of the region from an optical Doppler effect.

Doppler OCT has tomographic image information at different times and phase information included in the tomographic image information for the same region of the specimen. Meanwhile, according to the effect of optical Doppler, a frequency shift (change in frequency) of reflected light irradiated onto a mobile object corresponds to the speed of the object.

<Analysis Processing Unit>

The analysis processing unit (for example, the control unit 70) may be configured to process an OCT signal to generate motion contrast data in a specimen. Motion contrast is, for example, detection information of motion of the specimen, temporal change, or the like. For example, a flow image or the like is a kind of motion contrast. For example, the flow image detection represents motion of a fluid or the like in the form of an image. An angiographic image which images a blood vessel position obtained by detecting motion of blood is regarded as a kind of motion contrast. For example, the first image data generation unit may process a plurality of temporally different OCT signals with respect to the same position on the specimen. For example, the optical coherence tomography device 1 scans measurement light at least twice at the same position on the specimen to acquire temporally different OCT signals at the same position. It is preferable that the first image data generation unit acquires signals at the same position. However, the optical coherence tomography device 1 may not scan measurement light at the completely coincident position if positioning of acquired signals is subsequently performed. For example, adjacent scanning positions may be set. In this way, the same position includes adjacent scanning positions.

For example, the first image data generation unit may be configured to generate first image data, which is image data representing phase difference information in a plurality of OCT signals in the form of an image. First image data may be, for example, image data based on a Doppler OCT image (phase difference image) of Phase Difference, Phase variance, Doppler variance, or the like.

The second image data generation unit may be configured to process the OCT signals to generate second image data, which is image data representing information including the amplitude of the OCT signals in the form of an image. Second image data may be, for example, image data based on a vector difference (VD) of the OCT signals. In this case, for example, the second image data generation unit may process a plurality of temporally different OCT signals with respect to the same position on the specimen and may generate, as second image data, image data representing the difference between a first vector based on phase information and the amplitude information by a first OCT signal in the plurality of OCT signals and a second vector based on phase information and the amplitude information by a second OCT signal in the form of an image.

Second image data may be, for example, image data which is acquired by processing various OCT signals from Scattering OCT, Polarization Sensitive OCT, Stereoscopic OCT, or the like.

The analysis processing unit may be configured to generate motion contrast data based on the phase difference information in first image data generated by the first image data generation unit and information including the amplitude in second image data generated by the second image data generation unit.

Accordingly, it may be possible to acquire image data with high contrast and less unnecessary signals (artifact) compared to individual image data of first image data and second image data.

When generating motion contrast data based on first image data and second image data, the analysis processing unit uses various combinations of image data for first image data and second image data. For example, image data based on a Doppler OCT image (phase difference image) may be used as first image data, and a vector difference (VD) of an OCT signal may be used as second image data. For example, image data based on a Doppler OCT image (phase difference image) may be used as first image data, and image data obtained by processing an OCT signal acquired from Polarization Sensitive OCT or the like may be used as second image data.

When processing a plurality of OCT signals to generate motion contrast data, for example, the analysis processing unit may compute each set of first image data and second image data to create motion contrast data. For example, when one of first image data and second image data is one piece of image data obtained by processing a plurality of OCT signals, one piece of image data and the other piece computed for each set may be computed to generated motion contrast data. For example, both first image data and second image data may be respective pieces of image data obtained by processing a plurality of OCT signals, and two pieces of image data may be computed to generate motion contrast data.

The analysis processing unit may apply, to one piece of image data of first image data and second image data, a filter using the other piece of image data of the first image data and second image data to generate motion contrast data. Applying the filter is regarded as weighting the other piece of data to one piece of data. For example, first image data and second image data may be multiplied. For example, one piece of data may be binarized into "1" and "0" based on a threshold value, and may be multiplied by the other piece of data. Hereinafter, a kind of such filter processing is referred to as mask processing.

By performing the filter processing thus described, it may be possible to compensate for the disadvantages of both pieces of data with the advantages thereof and to acquire a satisfactory image.

The analysis processing unit may compute the phase difference information in first image data generated by the first image data generation unit and information including the amplitude in second image data generated by the second image data generation unit to obtain luminance with respect to each image of motion contrast data. For example, computation may be various types of computation, such as multiplication, division, addition, subtraction, and integration after multiplication or logarithm.

A program which causes the optical coherence tomography device 1 to execute the above-described processing may be stored in a storage medium. In this case, a processor (for example, the control unit 70) may cause the optical coherence tomography device 1 to execute the program stored in the storage medium.

EXAMPLE

Hereinafter, one typical example according to the illustrative embodiment will be described referring to the drawings. FIG. 1 is a block diagram illustrating the configuration of an optical coherence tomography device 1 according to this example.

The optical coherence tomography device (hereinafter, abbreviated as an OCT device) 1 processes a detection signal acquired by the OCT optical system 100. As an example, the OCT device according to the example is described as a fundus imaging device which acquires a tomographic image of a fundus oculi of a subject's eye.

Hereinafter, a configuration according to the example will be described referring to the drawings. FIG. 1 is a diagram showing the schematic configuration of the OCT device 1 according to this example. The OCT optical system 100 images a tomographic image from a fundus oculi Ef of a subject's eye E. The device may include an en-face observation optical system 200 and a fixation target projection unit 300. The OCT device 1 is connected to the control unit 70.

The OCT optical system 100 irradiates the fundus oculi with measurement light. The OCT optical system 100 detects an interference state of measurement light reflected from the fundus oculi and reference light by a light receiving element (detector 120). The OCT optical system 100 includes an irradiation position change unit (for example, an optical scanner 108 and a fixation target projection unit 300) which changes an irradiation position of measurement light on the fundus oculi Ef so as to change an imaging position on the fundus oculi Ef. The control unit 70 controls the operation of the irradiation position change unit based on the set imaging position information and acquires a tomographic image based on a light reception signal from the detector 120.

<OCT Optical System>

The OCT optical system 100 has the device configuration of a so-called optical tomography interferometer (OCT: Optical coherence tomography) for ophthalmology, and images the tomographic image of the eye E. The OCT optical system 100 splits light emitted from a measurement light source 102 into measurement light (sample light) and reference light by a coupler (light splitter) 104. The OCT optical system 100 guides measurement light to the fundus oculi Ef of the eye E by a measurement optical system 106 and guides reference light to a reference optical system 110. Thereafter, interference light by synthesis of measurement light reflected by the fundus oculi Ef and reference light is received by the detector (light receiving element) 120.

The detector 120 detects an interference signal of measurement light and reference light. In case of Fourier domain OCT, spectral intensity (spectral interference signal) of interference light is detected by the detector 120, and a complex OCT signal is acquired by Fourier transform of spectral intensity data. For example, the absolute value of the amplitude in the complex OCT signal is calculated to acquire a depth profile (A scan signal) in a predetermined range. The depth profile at each scanning position of measurement light scanned by the optical scanner 108 is arranged to acquire OCT image data (tomographic image data). Measurement light may be scanned in a two-dimensional manner to acquire OCT three-dimensional image data. An OCT en-face image (for example, an integrated image integrated with respect to a depth direction) may be acquired from OCT three-dimensional data.

A functional OCT signal may be acquired by analysis processing of the complex OCT signal. The functional OCT signal at each scanning position of measurement light scanned by the optical scanner 108 is arranged to acquire functional OCT image data. Measurement light may be scanned in a two-dimensional manner to acquire three-dimensional functional OCT image data. An OCT functional en-face image (for example, a Doppler en-face image or a signal image data spectral variance en-face image) may be acquired from three-dimensional functional OCT image data. The details will be described below.

For example, Spectral-domain OCT (SD-OCT) or Swept-source OCT (SS-OCT) may be exemplified. Time-domain OCT (TD-OCT) may be used.

In case of SD-OCT, a low-coherent light source (wide-band light source) is used as the light source 102, and the detector 120 is provided with a spectral optical system (spectrometer) which spectrally separates interference light into respective frequency components (respective wavelength components). The spectrometer has, for example, a diffraction grating and a line sensor.

In case of SS-OCT, a wavelength scanning light source (wavelength variable light source) which temporally changes an emission wavelength at high speed is used as the light source 102, and, for example, a single light receiving element is provided as the detector 120. The light source 102 has, for example, a light source, a fiber ring resonator, and a wavelength selection filter. For example, a combination of a diffraction grating and a polygon mirror or a filter using a Fabry-Perot etalon is exemplified as the wavelength selection filter.

Light emitted from the light source 102 is divided into a measurement light beam and a reference light beam by the coupler 104. The measurement light beam passes through an optical fiber and is then emitted to the air. The light beam is condensed on the fundus oculi Ef through other optical members of the optical scanner 108 and the measurement optical system 106. Light reflected by the fundus oculi Ef is returned to the optical fiber through the same optical path.

The optical scanner 108 scans measurement light on the fundus oculi in a two-dimensional manner (in the XY direction (transverse direction)). The optical scanner 108 is disposed at a position substantially conjugate to a pupil. The optical scanner 108 is, for example, two galvanomirrors, and the reflection angle thereof is arbitrarily adjusted by a driving mechanism 50.

Accordingly, a light beam emitted from the light source 102 is changed in the reflection (traveling) direction and is scanned in an arbitrary direction on the fundus oculi. With this, the imaging position on the fundus oculi Ef is changed. As the optical scanner 108, a configuration in which light is polarized may be made. For example, other than a reflection mirror (a galvanomirror, a polygon mirror, or a resonant scanner), an acoustic optical element (AOM) which changes the traveling (deflection) direction of light, or the like is used.

The reference optical system 110 generates reference light which is synthesized with reflected light acquired by reflection of the measurement light on the fundus oculi Ef. The reference optical system 110 may be of a Michelson type or a Mach-Zehnder type. For example, the reference optical system 110 is formed of a reflection optical system (for example, a reference mirror), reflects light from the coupler 104 by the reflection optical system to return light to the coupler 104 again, and guides light to the detector 120. As another example, the reference optical system 110 is formed of a transmission optical system (for example, an optical fiber), transmits light from the coupler 104 without returning light, and guides light to the detector 120.

The reference optical system 110 has a configuration in which an optical member in a reference light path moves to change an optical path length difference of measurement light and reference light. For example, the reference minor moves in an optical axis direction. A configuration for changing the optical path length difference may be disposed in the measurement light path of the measurement optical system 106.

<En-face Observation Optical System>

The en-face observation optical system 200 is provided so as to obtain an en-face image of the fundus oculi Ef. The observation optical system 200 includes, for example, an optical scanner which scans measurement light (for example, infrared light) emitted from the light source on the fundus oculi in a two-dimensional manner, and a second light receiving element which receives fundus reflected light through a confocal opening disposed at a position substantially conjugate to the fundus oculi, and has a device configuration of a so-called scanning laser ophthalmoscope (SLO) for ophthalmology.

As the configuration of the observation optical system 200, a so-called fundus camera type configuration may be used. The OCT optical system 100 may be also used as the observation optical system 200. That is, the en-face image may be acquired using data which forms the tomographic image obtained in a two-dimensional manner (for example, an integrated image in a depth direction of a three-dimensional tomographic image, an integrated value of spectrum data at each XY position, luminance data at each XY position in a given depth direction, a retinal surface image, or the like).

<Fixation target Projection Unit>

The fixation target projection unit 300 has an optical system which guides a visual line direction of the eye E. The projection unit 300 has a fixation target which is presented to the eye E, and can guide the eye E in a plurality of directions.

For example, the fixation target projection unit 300 has a visible light source which emits visible light, and changes a presentation position of a visual target in a two-dimensional manner. With this, the visual line direction is changed, and as a result, an imaging region is changed. For example, if the fixation target is presented from the same direction as the imaging optical axis, the center part of the fundus oculi is set as an imaging region. If the fixation target is presented upward with respect to the imaging optical axis, an upper part of the fundus oculi is set as an imaging region. That is, an imaging region is changed according to the position of the visual target with respect to the imaging optical axis.

As the fixation target projection unit 300, for example, a configuration in which a fixation position is adjusted by the turning-on positions of LEDs arranged in a matrix, a configuration in which light from a light source is scanned using an optical scanner and a fixation position is adjusted by turning-on control of the light source, and the like are considered. The projection unit 300 may be of an internal fixation lamp type or an external fixation lamp type.

<Control Unit>

The control unit 70 includes a CPU (processor), a RAM, a ROM, and the like. The CPU of the control unit 70 performs control of the entire device (OCT device 1, OCT optical system 100), for example, the members of the configurations 100 to 300. The RAM temporarily stores various types of information. The ROM of the control unit 70 stores various programs for controlling the operation of the entire device, initial values, and the like. The control unit 70 may be configured by a plurality of control units (that is, a plurality of processors).

A nonvolatile memory (storage unit) 72, a user interface (operation unit) 76, and a display unit (monitor) 75, and the like are electrically connected to the control unit 70. The nonvolatile memory (memory) 72 is a non-transitory storage medium which can hold the stored contents even if power supply is shut off. For example, a hard disk drive, a flash ROM, the OCT device 1, an USB memory which is detachably mounted in the OCT optical system 100, or the like can be used as the nonvolatile memory 72. The memory 72 stores an imaging control program for controlling imaging of an en-face image and a tomographic image by the OCT optical system 100. The memory 72 stores a fundus analysis program which allows the use of the OCT device 1. The memory 72 stores various types of information regarding imaging, such as a tomographic image (OCT data) in a scanning line, a three-dimensional tomographic image (three-dimensional OCT data), a fundus en-face image, and information of an imaging position of a tomographic image. Various operation instructions by an examiner are input to the user interface 76.

The user interface 76 outputs a signal according to an input operation instruction to the control unit 70. As the user interface 74, for example, at least one of a mouse, a joystick, a keyboard, a touch panel, and the like may be used.

A monitor 75 may be a display which is mounted in the device main body, or may be a display connected to the main body. A display of a personal computer (hereinafter, referred to as "PC") may be used. A plurality of displays may be used together. The monitor 75 may be a touch panel. When the monitor 75 is a touch panel, the monitor 75 functions as an user interface. Various images including a tomographic image and an en-face image imaged by the OCT optical system 100 are displayed on the monitor 75.

<Operation of Device, Acquisition of Interference Signal>

In the optical coherence tomography device 1, a tomographic image is acquired. Hereinafter, an imaging operation of the device will be described. The examiner instructs the subject to keep an eye on the fixation target of the fixation target projection unit 300 and then performs an alignment operation using the user interface 76 (for example, a joystick (not shown)) while viewing an anterior eye part observation image imaged by a camera for anterior eye part observation (not shown) on the monitor 75 such that a measurement optical axis is at the center of the pupil of the subject's eye.

Figure 3A:
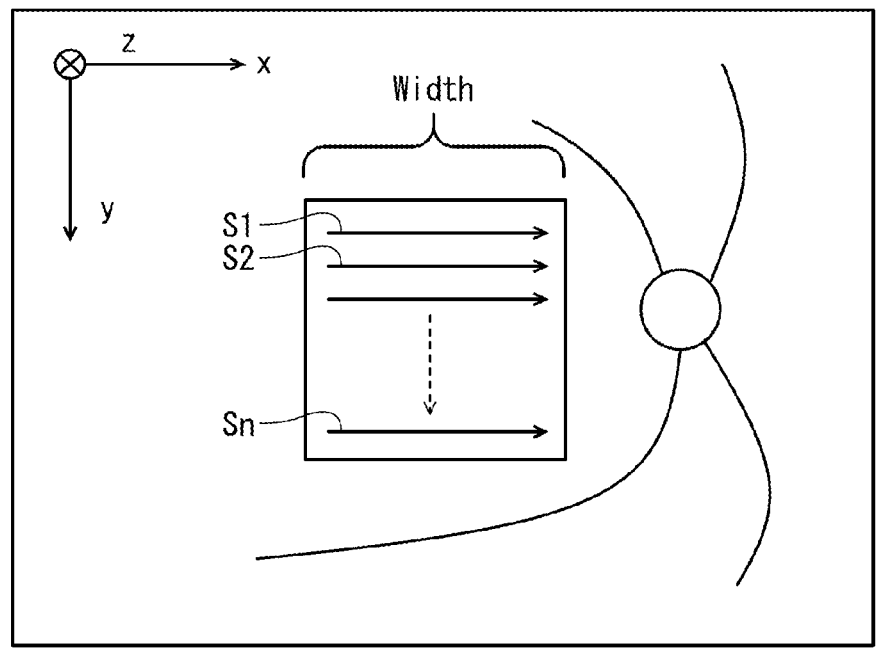
FIGS. 3A and 3B are image diagrams of a fundus oculi illustrating a measurement according to an example.

The control unit 70 acquires interference signals of at least two temporally different frames at the same position. For example, the control unit 70 controls the driving of the optical scanner 108 and scans measurement light on the fundus oculi. For example, measurement light is scanned in the x direction along a first scanning line S1 shown in FIG. 3A. Scanning of measurement light in the x direction is referred to as "B-scan". Hereinafter, an interference signal of one frame is described as an interference signal obtained by single B-Scan. The control unit 70 acquires an interference signal detected by the detector 120 during scanning. In FIG. 3A, the direction of a z axis is referred to as the direction of the optical axis of measurement light. The direction of the x axis is referred to as the direction perpendicular to the z axis and right and left. The direction of the y axis is referred to as the direction perpendicular to the z axis and up and down.

Figure 3B:
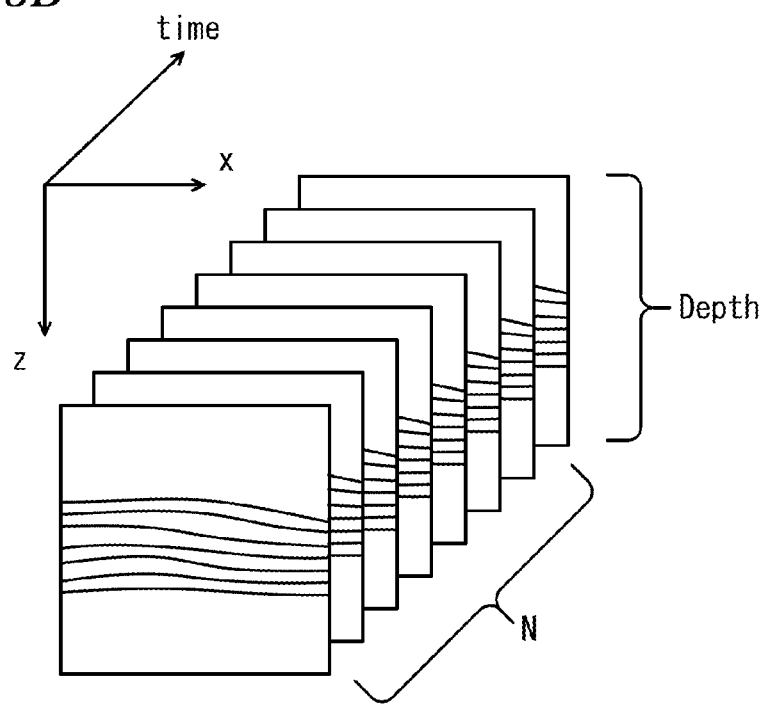

When the first scanning is completed, the control unit 70 performs second scanning at the same position as the first scanning. For example, the control unit 70 scans measurement light along the scanning line S1 shown in FIG. 3A and scans measurement light again. The control unit 70 acquires an interference signal detected by the detector 120 during the second scanning. Accordingly, the control unit 70 can acquire interference signals of two temporally different frames at the same position. In this example, scanning at the same position is repeated eight times, and interference signals of eight temporally different continuous frames are acquired. For example, as shown in FIG. 3B, scanning in the scanning line S1 is repeated eight times, and interference signals of eight frames are acquired.

When temporally different interference signals at the same position can be acquired by single scanning, the second scanning may not be performed. For example, when two beams of measurement light with deviation in optical axis by a predetermined interval are scanned at one time, it is not necessary to perform scanning multiple times. It should suffice that temporally different interference signals at the same position in the subject can be acquired. When two beams of measurement light are scanned at one time, it is possible to detect an arbitrary blood flow rate as an objective by the interval between two beams of measurement light.

Similarly, the control unit 70 may acquire signals of at least two temporally different frames at another position. As shown in FIG. 3A, a first scanning line S1 is, for example, y=y1. A second scanning line S2 is, for example, y=y2. If the acquisition of temporally different signals in the first scanning line S1 is completed, the control unit 70 may successively signals of at least two temporally different frames in the second scanning line S2.

The control unit 70 thus acquires signals at different times of the subject. For example, in this example, scanning is repeated eight times in the same line, and interference signals of eight frames are acquired. However, the number of frames is not limited to eight frames, and it should suffice that interference signals of at least two temporally different frames are acquired.

As shown in FIG. 3A, the control unit 70 raster-scans measurement light and obtains interference signals of at least two temporally different frames in each scanning line. Accordingly, it is possible to acquire three-dimensional information inside a fundus oculi.

Raster scanning is a pattern in which measurement light is scanned on a fundus oculi in a rectangular shape. Raster scanning is used as, for example, OCT functional en-face image scanning In raster scanning, for example, measurement light is rasterized in a scanning region (for example, a rectangular region) set in advance. As a result, a tomographic image in each scanning line is acquired inside the scanning region (for example, the rectangular region).

As scanning conditions in raster scanning, for example, a line width (the distance between a start point and an end point) in each of a main scanning direction and a sub scanning direction, a scanning speed, the interval between the scanning lines, the number of scanning lines, and the like are set in advance. The scanning conditions in raster scanning may be set arbitrarily.

In more detail, the control unit 70 scans measurement light in the main scanning direction in a scanning line (first line) set as a start position to functional OCT image data along the main scanning direction. Next, the control unit 70 scans measurement light in the main scanning direction in a different scanning line with respect to the sub scanning direction to form functional OCT image data along the main scanning direction. As described above, functional OCT image data is obtained with respect to N different lines. Each scanning interval with respect to the sub scanning direction is narrowed, whereby functional OCT image data can be acquired in the scanning region. The scanning region is formed by different scanning lines with respect to the sub scanning direction.

In the following description, an example where the sub scanning direction is set as the y direction (up-down direction) and the main scanning direction is set as the x direction (right-left direction) has been described, the present disclosure is not limited thereto. For example, the sub scanning direction may be the x direction and the main scanning direction may be the y direction.

In regards to scanning control in the sub scanning direction, a scanning position may be changed in order from top to bottom or may be changed in order from bottom to top. The scanning position may be changed in order from the center to the periphery. As raster scanning, an interlace system may be used.

When acquiring temporally different interference signals at the same position, for example, the control unit 70 scans measurement light in the main scanning direction multiple times in the first scanning line S1. That is, after the first scanning from the start point to the end point ends in the first scanning line S1, the control unit 70 returns the scanning position of measurement light to the start point in the first scanning line S1 again and performs scanning in the first scanning line S1 again.

The control unit 70 generates functional OCT image data (for example, motion contrast data) corresponding to the first scanning line S1 based on an output signal from the detector 120. Functional OCT image data is acquired by multiple scanning to the same scanning position. For example, the control unit 70 performs scanning the first scanning line S1 until functional OCT image data of the number of frames set in advance is obtained.

After multiple scanning in the first scanning line S1 ends, the control unit 70 performs control such that the optical scanner 108 scans measurement light in the main scanning direction multiple times in the second scanning line S2. The control unit 70 generates functional OCT image data corresponding to the second scanning line S2. For example, the control unit 70 performs scanning in the second scanning line S2 until functional OCT image data of the number of frames set in advance is obtained.

Similarly, the control unit 70 scans measurement light multiple times in each scanning line up to the last scanning line Sn to generate functional OCT image data corresponding to each scanning line. That is, in the second scanning control, scanning is performed multiple times in each scanning line.

The control unit 70 may perform control such that the OCT optical system 100 acquires the interference signal and may perform control such that the observation optical system 200 acquires the fundus en-face image.

<Signal Processing Method>

Figure 4:
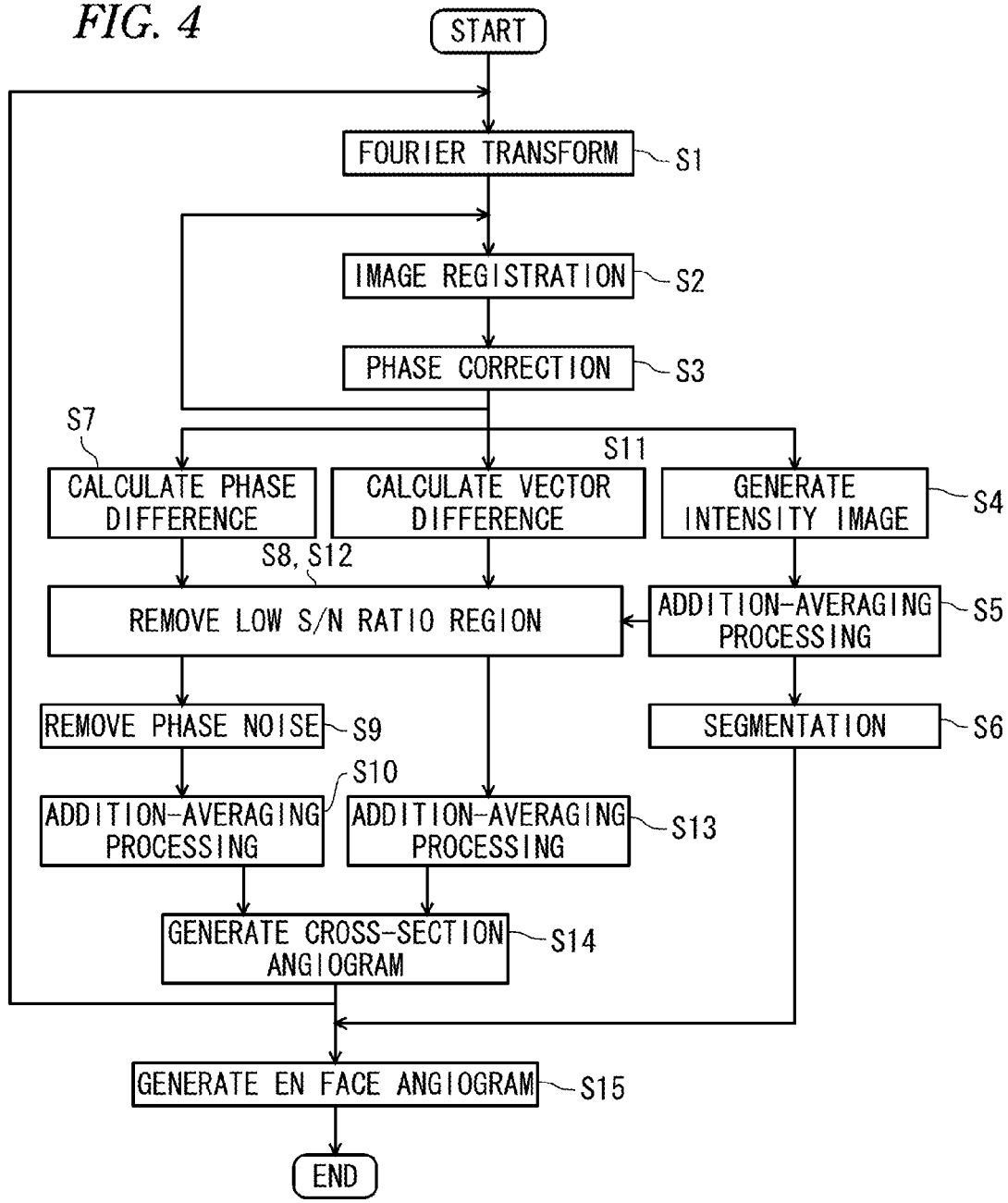
FIG. 4 is a flowchart illustrating processing according to the example.

A signal processing according to the example will be described referring to FIG. 4. The control unit 70 includes a processor (for example, a CPU) which controls various types of control processing, and a storage medium which stores a program. The processor executes processing described below according to the program. Processing of Steps 7 to 10 described below is processing regarding a Doppler phase difference method. Processing of Steps 11 to 13 is processing regarding a vector difference method. In the following description, although a number for identifying each step of control is given, the given number does not necessarily match the number of actual control. In the following description, a signal at an n-th position (x,z) in an N frame is expressed by An (x,z).

(Step 1: Fourier transform)

First, the control unit 70 performs Fourier transform of interference signal acquired by the OCT optical system. The control unit 70 obtains a complex OCT signal An (x,z) by Fourier transform. The complex OCT signal An (x,z) includes a real component and an imaginary component.

(Step 2: Image registration)

In order to obtain a blood flow signal, it is necessary to compare temporally different images at the same position. For this reason, it is preferable that the control unit 70 performs positioning of images based on image information (see FIGS. 5A and 5B). Image registration is a process in which a plurality of images in the same scene are arranged in alignment. As a factor for deviation in the position of the image, for example, motion of the subject's eye during imaging is considered.

(Step 3: Phase correction)

Figure 6:
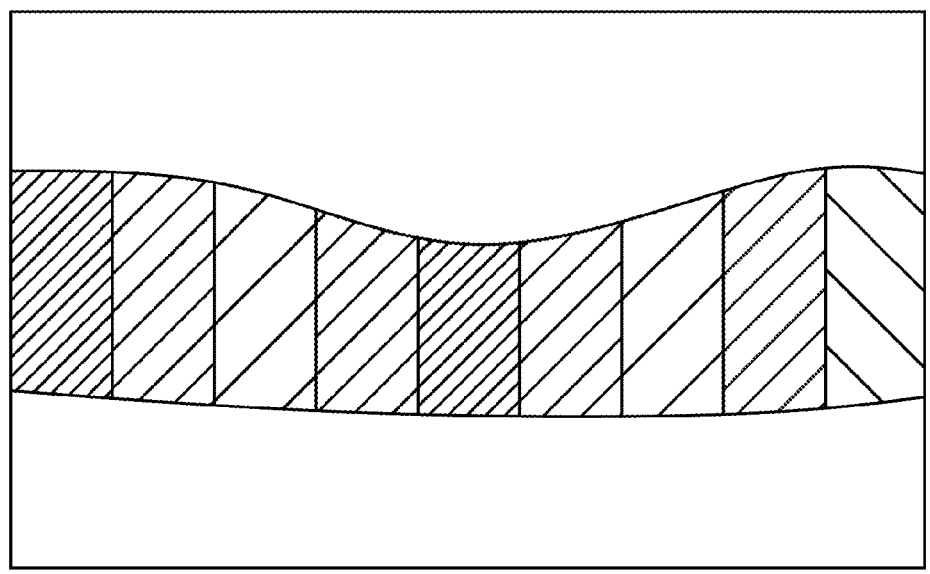
FIG. 6 is a diagram showing a mode in which a phase difference of a non-vascular part is different for each A-Line.

In Step 2, even if positioning between frames is performed, phase deviation may occur between A-Lines in the same image (see FIG. 6). Accordingly, it is preferable to perform phase correction.

The control unit 70 repeatedly performs Steps 2 and 3 for each frame. The processing of Steps 2 and 3 is provided to easily perform the processing according to the example, and is not necessarily essential.

(Step 4: Generation of intensity image)

The control unit 70 acquires intensity information of the acquired complex OCT signal. Signal intensity In (x,z) is expressed by Expression (1).

$$I_n(x,z) = |A_n(x,z)|^2 \qquad (1)$$

For example, the control unit 70 converts intensity information to brightness to generate image data. For example, a region with large intensity is expressed bright, and a region with small intensity is expressed dark. In this way, in the description according to the example, an image which expresses intensity information as information of brightness is referred to as an intensity image.

(Step 5: Noise reduction by addition-averaging processing of intensity image)

The control unit 70 acquires a plurality (for example, eight) of intensity images in Step 4. The control unit 70 adds and averages a plurality of intensity images using Expression (2). Accordingly, spectral noise or the like in each frame is reduced. For example, since a signal based on measurement light reflected by a retinal layer is detected with the substantially same value in a plurality of images, there is no significant change even after addition-averaging. Since there is a noise component randomly in eight images, the intensity of the noise component becomes small compared to a signal component.

$$I_n(x,z) = \frac{1}{N}\sum_{n=1}^{N} I_n(x,z) \qquad (2)$$

(Step 6: Segmentation)

The control unit 70 detects the boundary of each retinal layer from the image subjected to addition-averaging and divides a cell region. For example, the cell region is classified into a nerve fiber layer (NFL), a ganglion cell layer (GCL), a retinal pigment epithelium (RPE), and the like.

(Step 7: Calculation of phase difference)

Figure 7:
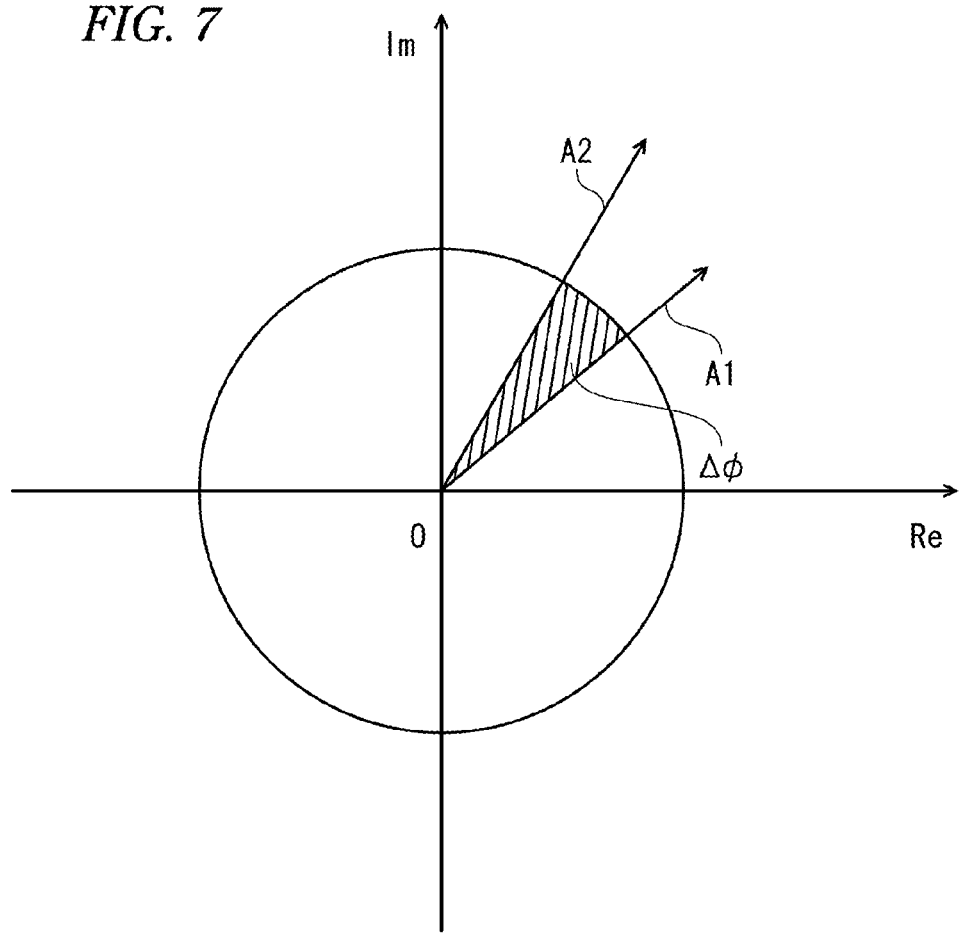
FIG. 7 is a diagram illustrating a phase difference.

Next, the control unit 70 calculates the phase difference between OCT signals A(x,z) acquired at two or more different times at the same position. For example, as shown in FIG. 7, a signal measured at the time T1 is referred to as a signal A1, and a signal measured at the time T2 is referred to as a signal A2. The control unit 70 calculates temporal change in phase using Expression (3). In this example, for example, since measurement is performed at eight different times, calculation is performed at T1 and T2, T2 and T3, T3 and T4, T4 and T5, T5 and T6, T6 and T7, and T7 and T8 seven times in total, and seven pieces of data are calculated. The symbol "*" in the expression represents a complex conjugate.

$$\Delta\varphi_n(x,z) = \arg(A_{n+1}(x,z) \times A_n^*(x,z)) \qquad (3)$$

(Step 8: Removal of part with low S/N ratio)

Figure 8:
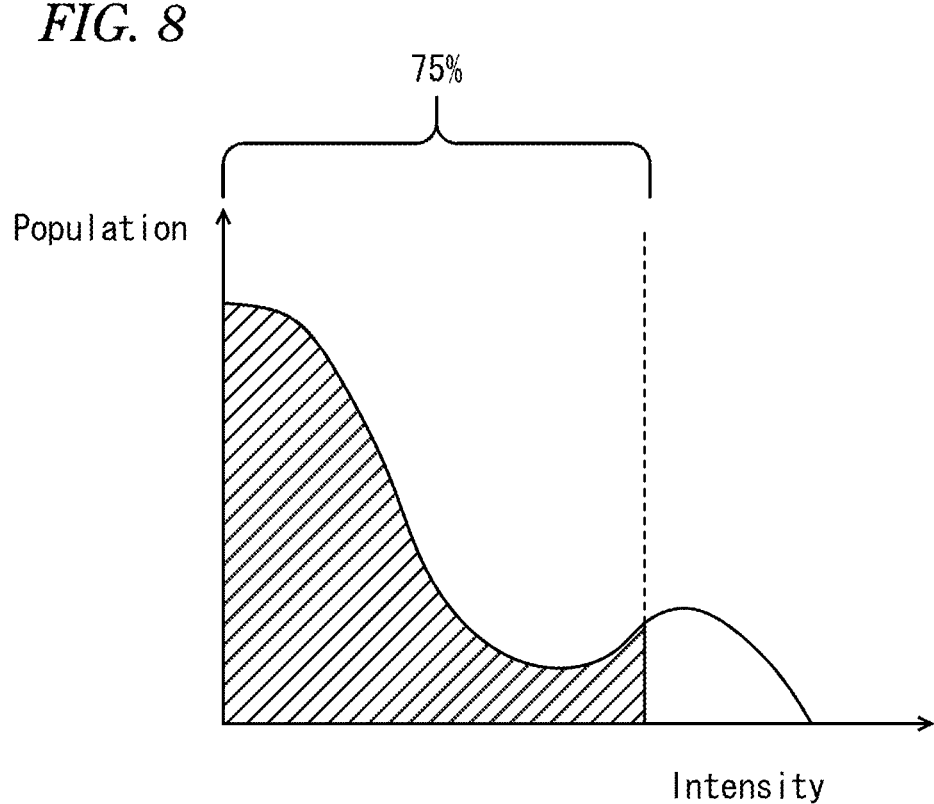
FIG. 8 is a diagram illustrating a denoising method.

The control unit 70 removes a random phase difference in a region with low signal-to-noise ratio (S/N ratio). For example, the control unit 70 creates a histogram of intensity shown in FIG. 8 and searches for a threshold value at which a cumulative value becomes 75%. The control unit 70 sets the values of a phase difference and a vector difference of a region (a hatched region of FIG. 8) with intensity less than the threshold value to 0. Accordingly, image noise is reduced.

(Step 9: Removal of part with small phase difference)

The control unit 70 removes a part with a small phase difference. This is to remove a reflection signal from a high reflection part, such as a nerve fiber layer (NFL). Accordingly, it becomes easy to distinguish whether a signal is a signal from a high reflection part or a signal from a blood vessel.

(Step 10: Denoising by addition-averaging processing)

The control unit 70 adds and averages signals of seven frames subjected to the above-described processing and removes noise. For example, the control unit 70 performs addition-averaging processing using expression (4).

$$|\Delta\phi(x,z)| = \frac{1}{N-1}\sum_{n=1}^{N-1} |\Delta\phi_n(x,z)| \qquad (4)$$

(Step 11: Calculation of vector difference)

Figure 9:
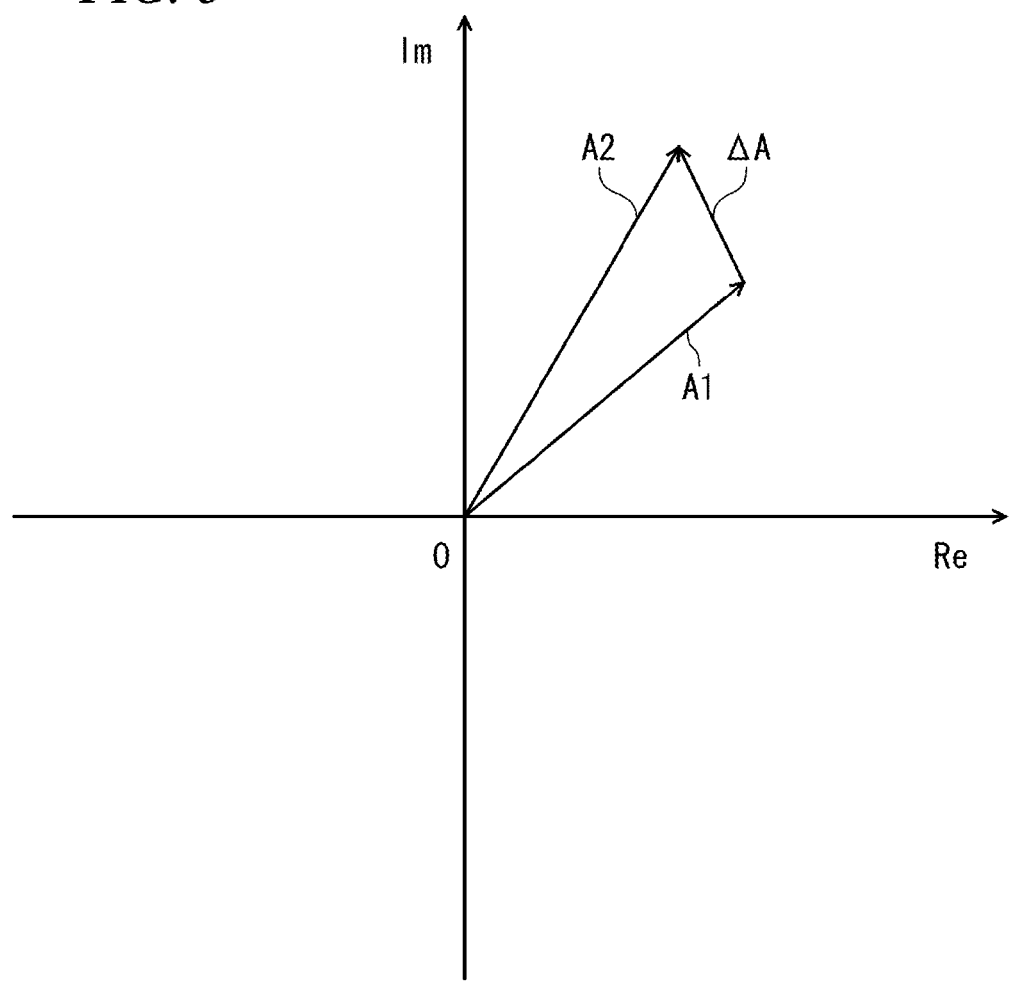
FIG. 9 is a diagram illustrating a vector difference.

Subsequently, the vector difference will be described. The vector difference of complex OCT signals detected by the OCT optical system is calculated. For example, as in FIG. 9, a complex OCT signal can be represented as a vector on a complex plane. Accordingly, signals A1 and A2 at the same position are detected at certain times T1 and T2, and a vector difference AA is calculated by Expression (5), thereby generating contrast image data in the subject. When imaging the vector difference ΔA, for example, imaging may be performed based on phase information, in addition to the magnitude of the difference ΔA.

$$|\Delta A_n(x,z)|=|A_{n+1}(x,z)-A_n(x,z)| \quad (5)$$

(Step 12: Removal of low S/N ratio part)

Similarly to Step 8, a random phase difference component in a region with low S/N ratio is removed.

(Step 13: Addition-averaging processing)

The control unit 70 adds and averages signals for seven frames subjected to the above-described processing and removes noise. For example, the control unit 70 performs addition-averaging processing of the vector difference using Expression (6).

$$|\Delta A(x,z)| = \frac{1}{N-1}\sum_{n=1}^{N-1}|\Delta A_n(x,z)| \quad (6)$$

(Step 14: Multiply images. Apply filter)

The control unit 70 uses a calculation result of a phase difference as a filter to a calculation result of a vector difference. In the description according to the example, for example, "apply filter" performs weighting to a certain numerical value. For example, the control unit 70 performs weighting by multiplying the calculation result of the vector difference by the calculation result of the phase difference. That is, a vector difference of a part with a small phase difference is weakened, and a vector difference of a part with a large phase difference is strengthened. Accordingly, the calculation result of the vector difference is weighted to the calculation result of the phase difference.

In the processing according to the example, the control unit 70 multiplies the calculation result of the vector difference and the calculation result of the phase difference. For example, the control unit 70 multiplies the calculation result of the vector difference and the calculation result of the phase difference using Expression (7). Accordingly, the control unit 70 generates a cross-section angiogram CA which is weighted by the calculation result of the phase difference.

The calculation result of the vector difference and the calculation result of the phase difference are multiplied, whereby it is possible to cancel the disadvantages of the respective measurement methods and to skillfully detect an image of a vascular part.

For example, as described above, when the PD method is used, a blood vessel and a background part are detected strongly. A high reflection part, such as an NFL, is detected weakly (see FIG. 10). This is because the blood vessel and the background part have large fluctuation in phase, and the high reflection part, such as an NFL, has small fluctuation in phase.

Figure 11:
FIG. 11 is a diagram showing an image obtained by a vector difference method.

When the VD method is used, a blood vessel is detected strongly, a background part is detected weakly, a high reflection part, such as an NFL, is detected more weakly than the blood vessel and more strongly than the background part (see FIG. 11). This is because the blood vessel has fluctuation in amplitude and phase of an OCT signal; the background part has small fluctuation in amplitude and small fluctuation in phase; and the high reflection part, such as an NFL, has small fluctuation in phase and has large fluctuation in amplitude.

Figure 12:
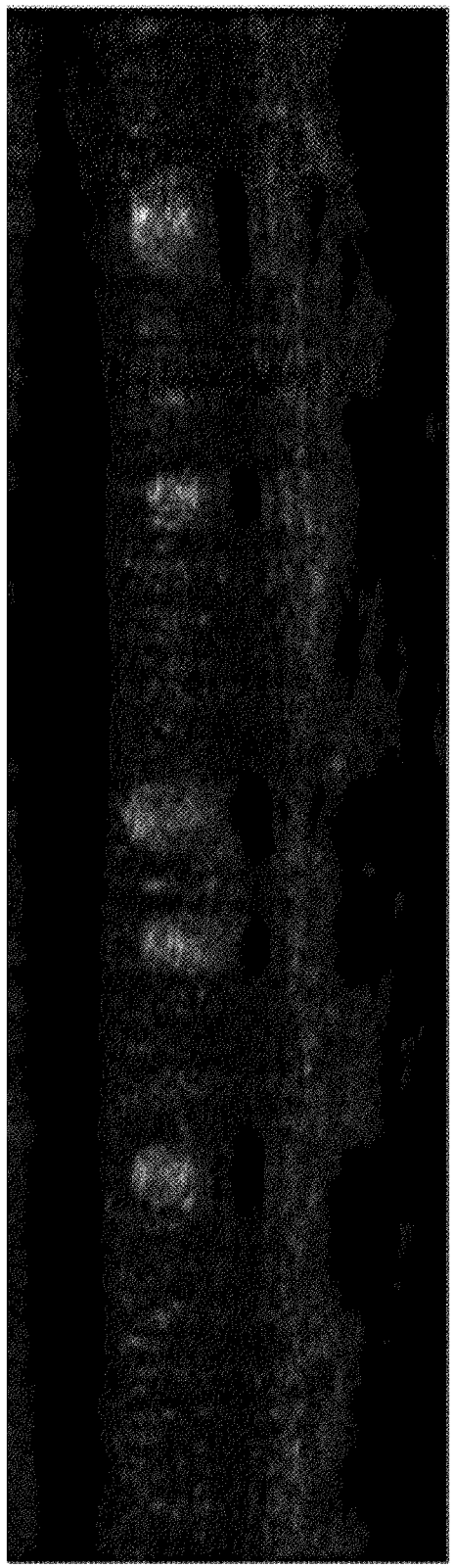
FIG. 12 is a diagram showing an image obtained by a vector difference method using a Doppler filter.

When two types of motion contrast are multiplied, since the vascular part is detected strongly using any method, the vascular part is detected strongly after multiplication. Since the background part is detected strongly in the PD method, but is detected weakly in the VD method, the background part is detected weakly after multiplication. Since the high reflection part, such as NFL, is detected strongly to a certain degree in the VD method, but is detected weakly in the PD method, the high reflection part is detected weakly after multiplication. In this way, the calculation result of the PD method and the calculation result of the VD method are multiplied, whereby only the vascular part is detected strongly. Two signals are multiplied, whereby it is possible to remove an artifact which is detected in each of the PD method and the VD method (see FIG. 12).

The control unit 70 repeats Steps 1 to 14 for each scanning line and generates the cross-section angiogram CA for each scanning line.

$$CA(x,z)=|\Delta\varphi(x,z)|\times|\Delta A(x,z)| \quad (7)$$

(Step 15: Add in z direction for each layer of fundus oculi to generate en-face image.)

The control unit 70 integrates the cross-section angiogram CA obtained from Expression (7) in the z direction for each layer of the fundus oculi divided by segmentation of Step 6 to generate an en-face angiogram EA. For example, when generating an integrated image from an inner limiting membrane (ILM) of the fundus oculi to a visual cell inner segment-outer segment joint (IS/OS), Expression (8) is used.

$$EA(x,y)=\int_{ILM}^{IS/OS}CA(x,y,z)dz \quad (8)$$

Figure 13:
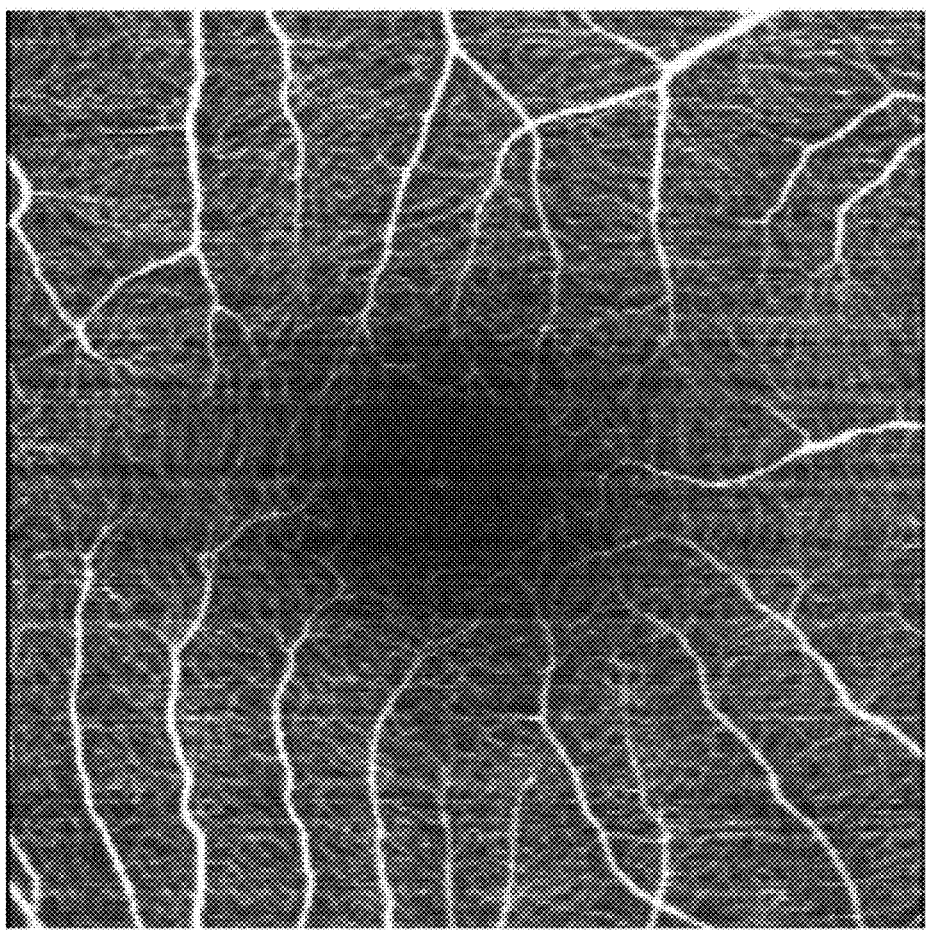
FIG. 13 is a diagram showing an en-face image obtained by a vector difference method using a Doppler filter.

The control unit 70 performs the above-described processing to generate an angiographic image shown in FIG. 13. The control unit 70 may display the generated image on the display unit. Data may be transferred to other devices.

In this example, functional OCT image data of the subject is thus acquired using at least two methods including the signal processing method using the phase difference and the signal processing method using the vector difference. Accordingly, it is possible to acquire a more vivid image by compensating for the advantages and disadvantages of the respective measurements.

For example, conventional fluorescein fluorescence fundus angiography (FA) and the like can only generate a fully integrated image. However, in the optical coherence tomography device 1 according to the example, it is possible to generate an image integrated in each retinal layer. Accordingly, it is possible to observe a blood vessel by retinal layer. The type of a blood vessel is different by retinal layer. For example, there are many blood vessels, called a surface capillary of a retina, in a nerve fiber layer, and there are many blood vessels, called a deep capillary, in an inner granular layer. For this reason, it is preferable to observe an adequate retinal layer based on a diagnostic item.

It is possible to achieve three-dimensional visualization by volume data of a vascular structure. In the method according to the example, since an artifact or the like in the shadow of the blood vessel is reduced, it is possible to acquire a satisfactory three-dimensional image.

Modification Example of First Example

In Step 14, although the calculation result of the vector difference and the calculation result of the phase difference are multiplied, the present disclosure is not limited thereto. For example, a mask based on the calculation result of the phase difference may be used to the vector difference. In this embodiment, "mask" is, for example, processing in which a value greater than a certain threshold value is used as it is, and a value smaller than a certain threshold value is set to "0". Accordingly, when a mask based on the phase difference is used, for example, the control unit 70 applies "0" to the calculation result of the vector difference in a region where the phase difference is equal to or less than 0.4 radian. The control unit 70 applies "1" to the calculation result of the vector difference in a region where the phase difference is equal to or greater than 0.4 radian.

In the mask generated based on the calculation result of the phase difference, a high reflection part, such as an NFL or a RPE, with less signals becomes "0". For this reason, the control unit 70 can set a signal of a high reflection part to be a problem in the VD method to 0, thereby decreasing signals of unnecessary parts other than a blood vessel.

In the above description, although a PD filter or the like is used in the VD method, the present disclosure is not limited thereto. For example, a PD filter or the like may be used to the result obtained for the above-described spectral variance. A Doppler filter or the like may be used to an addition average of intensity.

In the above description, although two signals (image data) are multiplied, two or more signals may be multiplied. For example, three signals may be multiplied. For example, a signal for DOPU (degree of polarization uniformity) or the like may be multiplied. The DOPU is a value representing polarization uniformity. That is, the device may multiply at least two of a plurality of pieces of functional OCT image data and image data to generate a new functional OCT image.

The control unit 70 may be configured to apply a filter, based on the calculation result of the phase difference, onto the image data obtained from the OCT signal, which may contain complex images and image data based on the vector difference. For example, the control unit 70 may apply a filter on a pixel having smaller calculation result of the phase difference to lessen signal intensity in the image data. The control unit 70 may apply a filter on a pixel having larger calculation result of the phase difference to enlarge signal intensity in the image data. The control unit 70 may be configured to adjust the correction ratio of the signal intensity according to the calculation result of the phase difference, or may be configured to apply the same correction ratio of the signal intensity, when applying the filter.

Second Example

Hereinafter, a second example will be described for a part different from the first example. In the first example, the control unit 70 uses the result in the PD method as the filter or the like. In the second example, the control unit 70 uses a measurement result in the VD method as a mask. For example, in the second example, the measurement result in the VD method is used as a mask to a measurement result in the PD method.

Accordingly, in the second example, similarly to the first example, it is possible to acquire a more vivid image by compensating for the advantages and disadvantages of the PD method and the VD method.

In a method of detecting a vector difference, information correlated with the blood flow rate is not obtained. However, a Doppler phase angle is correlated with speed. In a method which uses a VD mask to the result of the PD method, information of a Doppler phase angle is left. Therefore, the control unit 70 can obtain the blood flow rate. If the blood flow rate can be obtained, it is possible to perform diagnosis of various diseases.

What is claimed is:

1. An optical coherence tomography device comprising:
   an OCT optical system configured to detect measurement light irradiated onto a specimen and a reference light and output OCT signal based on the measurement light and the reference light; and
   an analysis processing unit configured to process the OCT signal and generate functional OCT data of the specimen,
   wherein the analysis processing unit comprises:
   a first image data generation unit configured to generate first functional OCT image data by applying first analysis processing on the OCT signal; and
   a second image data generation unit configured to generate second functional OCT image data by applying second analysis processing that is different from the first analysis processing on the OCT signal, and
   wherein the analysis processing unit generates the functional OCT image data based on the first functional OCT image data generated by the first image data generation unit and the second functional OCT image data generated by the second image data generation unit,
   wherein the first functional image data is based on a vector difference of a complex OCT signal, and
   wherein the second functional OCT image data is based on decorrelation of an intensity signal; and
   wherein the analysis processing unit applies the second functional OCT image data as a filter onto the first functional OCT image data to remove an artifact at a detected high reflection portion.

2. The optical coherence tomography device according to claim 1, wherein the analysis processing unit applies to the first functional image data a weight based on the second functional image data.

3. The optical coherence tomography device according to claim 1, wherein the high reflection portion is a nerve fiber layer (NFL).

* * * * *